United States Patent [19]

Chandran et al.

[11] Patent Number: 5,632,977
[45] Date of Patent: *May 27, 1997

[54] HAIR CARE COMPOSITIONS CONTAINING POLYMERIC N-VINYL FORMAMIDE AND METHODS OF TREATING HAIR

[75] Inventors: Rama S. Chandran, Bridgewater; Jean-Pierre Leblanc, Somerville; John C. Leighton, Flanders; Gary T. Martino, Plainsboro, all of N.J.

[73] Assignee: National Starch and Chemical Investment Holding Corporation, Wilmington, Del.

[*] Notice: The term of this patent shall not extend beyond the expiration date of Pat. No. 5,478,553.

[21] Appl. No.: 510,987

[22] Filed: Aug. 3, 1995

Related U.S. Application Data

[63] Continuation-in-part of Ser. No. 286,850, Aug. 5, 1994, Pat. No. 5,478,553, and a continuation-in-part of Ser. No. 417,358, Apr. 5, 1995, and a continuation-in-part of Ser. No. 417,369, Apr. 5, 1995, Pat. No. 5,609,857.

[51] Int. Cl.⁶ .................................................. A61K 7/075
[52] U.S. Cl. ...................... 424/70.17; 424/78.35
[58] Field of Search ........................ 424/70.17, 78.35

[56] References Cited

U.S. PATENT DOCUMENTS

| | | | |
|---|---|---|---|
| Re. 34,713 | 8/1994 | Itagaki et al. | 525/328.4 |
| 2,628,224 | 1/1953 | Le Sueur Cairns et al. | 260/89.7 |
| 3,212,972 | 10/1965 | Bailey, Jr. | 167/87.1 |
| 4,240,450 | 12/1980 | Grollier et al. | 132/7 |
| 4,402,977 | 9/1983 | Grollier et al. | 424/70 |
| 4,421,602 | 12/1983 | Brunnmueller et al. | 162/168.2 |
| 4,578,515 | 3/1986 | Dawson et al. | 564/215 |
| 4,623,699 | 11/1986 | Brunnmueller et al. | 525/355 |
| 4,713,236 | 12/1987 | Hoover et al. | 528/325 |
| 4,906,777 | 3/1990 | Pinschmidt, Jr. et al. | 564/215 |
| 4,942,259 | 7/1990 | Parris et al. | 564/187 |
| 5,021,238 | 6/1991 | Martino et al. | 424/47 |
| 5,037,927 | 8/1991 | Itagaki et al. | 526/307.7 |
| 5,037,930 | 8/1991 | Shih | 527/301 |
| 5,064,909 | 11/1991 | Itagaki et al. | 525/340 |
| 5,262,008 | 11/1993 | Moench et al. | |
| 5,270,379 | 12/1993 | McAndrew et al. | 524/555 |
| 5,373,076 | 12/1994 | Pinschmidt et al. | 526/303.1 |
| 5,478,553 | 12/1995 | Chandron et al. | 424/70.17 |

FOREIGN PATENT DOCUMENTS 2040601  4/1991  Canada.

OTHER PUBLICATIONS

Vinamer™ EF–Experimental Monomer for Amide–and Amine–Functional Polymer Systems, Information Bulletin.

*Primary Examiner*—Peter F. Kulkosky
*Attorney, Agent, or Firm*—William K. Wissing

[57] ABSTRACT

The present invention relates to hair care compositions which contain a polymer which is prepared from N-vinyl formamide (NVF) monomer and the use of those hair care compositions to treat hair. The polymer may be a homopolymer of NVF or an interpolymer of NVF and at least one vinyl monomer. The polymer is present in amounts effective to provide the hair care compositions with hair fixative properties and/or hair conditioning properties.

22 Claims, No Drawings

HAIR CARE COMPOSITIONS CONTAINING POLYMERIC N-VINYL FORMAMIDE AND METHODS OF TREATING HAIR

This application is a continuation-in-part of U.S. patent applications, Ser. Nos. 08/286,850, filed Aug. 5, 1994 now U.S. Pat. No. 5,478,553, 08/417,358 pending, filed Apr. 5, 1955 and 08/417,369, filed Apr. 5, 1995 now U.S. Pat. 5,609,857.

FIELD OF THE INVENTION

This invention relates to hair care compositions which comprise a polymer prepared from N-vinyl formamide monomer.

BACKGROUND OF THE INVENTION

In their most basic form, hair care compositions contain a film-forming resin, typically a polymer. The resin can be applied to the hair in the form of a spray, a gel, a mousse, a rinse, a lotion, a conditioner or a shampoo.

In aerosol hair spray systems, the resin usually is dissolved in an organic solvent, such as ethanol or isopropyl alcohol, and delivered via a propellant, which is usually a volatile hydrocarbon. These systems are becoming less desirable due to the consumers perception that alcohol in hair sprays can dry and damage hair, and due to environmental regulations limiting the emission of volatile organic compounds (VOC) into the atmosphere. As used herein, a volatile organic compound is an organic compound containing from 1 to 10 carbon atoms, and which has a vapor pressure of at least 0.1 mm Hg at 20° C. There is an on-going effort by the hair care industry to replace VOC with water. However, the inclusion of significant amounts of water in hair fixative compositions has created problems relating to solubility and dispersability of the hair fixative resin in the compositions, to application of the hair fixatives to the hair and to performance of the hair fixative once applied to the hair.

There is a need in the industry for low VOC, aqueous-based, hair fixative compositions and hair fixative polymers which are dispersable or soluble in water, which can be applied readily to the hair, and which provide acceptable hair fixative properties, such as strength, i.e., holding power or stiffness, humidity resistance, film clarity, aesthetics and removability from hair using conventional shampoo and/or water.

One such approach to lower VOC hair fixatives is disclosed in U.S. Pat. No. 5,021,238, in the name of Martino et al. Two-phase, aqueous-based, hair-fixing aerosol systems which utilize dimethyl ether as a propellant are disclosed. The system can be shaken to form a semi-stable emulsion or mixture which is stable for a time sufficient for spraying.

Another approach to significantly reducing or totally eliminating VOC in hair fixatives is the use of water-dispersable or water-soluble polymers in an aqueous-based hair fixative gel. Such gels which are available currently utilize poly(vinyl pyrrolidone) (PVP) or derivatives thereof, such as poly(vinyl pyrrolidone/vinyl acetate) copolymers (PVP/VA), as the hair fixative resin contained therein. PVP is very sensitive to water or humidity, which deteriorates the fixative properties. It is desirable, then, to find a water-soluble polymer to replace PVP. The polymer should be less sensitive to water, form clear films upon drying, and provide the hair fixative gels with hair fixative properties which are as good as or better than hair fixative gels which contain PVP as the fixative resin.

Hair conditioning agents are functional additives used in hair care products such as lotions, shampoos, creme rinses, mousses and setting gels to improve the tactile and physical properties of hair. Cationic quaternary ammonium compounds, both mono-and di-functional, low molecular weight quaternary ammonium salts and certain high molecular weight polymers, are employed as conditioning additives in hair care products such as shampoos, conditioners, creme rinses, mousses, sprays and setting gels to impart wet and dry combability, improve feel, enhance curl retention and impart antistatic properties to hair. The Cosmetics, Toiletries and Fragrances Association (INCI) has established a designation index for compounds employed in cosmetic and toiletry products. Two low molecular weight quaternary ammonium compounds that are commonly used in hair care products because of their low cost are stearylbenzyldimethylammonium chloride (INCI designation—stearalkonium chloride) and cetyltrimethylammonium chloride (INCI designation—cetrimonium chloride).

The high molecular weight, cationic quaternary ammonium polymers (polyquats) are being used increasingly in hair care products because of their reported advantages over the simple quaternary ammonium salts in enhancing wet combability, mending split ends and improving appearance. Commonly used polyquats include: UCARE™ Polymer JR (INCI designation—Polyquaternium 10) from Union Carbide, a quaternized cellulose; Gafquat™ (INCI designation—Polyquaternium 11)from International Specialty Products, a quaternized copolymer of vinylpyrrolidone and dimethylaminoethyl methacrylate; and Merquat™ 550 (Polyquaternium 7) from Calgon, a homopolymer of dimethyldiallylammonium chloride.

These quaternary ammonium conditioning additives have in common the quaternary ammonium functional group:

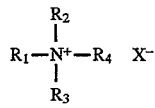

where $R_1$ through $R_4$ may be various substituted or unsubstituted alkyl or aryl substituents, or in the case of the polyquats, represent alkylene or arylene segments of a polymer chain. Associated with the positively charged quaternary ammonium nitrogen atom is a negatively charged counterion. This anion, $X^{31}$ may be a halide, hydroxide, methylsulfate or similar negatively charged group.

While it is known that copolymers of vinylpyrrolidone and quaternary ammonium compounds are used as hair conditioning additives in hair conditioning compositions, it is desirable to develop new polymers which can be used as a hair conditioning additive.

SUMMARY OF THE INVENTION

The present invention relates to hair care compositions which comprise a polymer which is prepared from N-vinyl formamide (NVF) monomer. The polymer may be a homopolymer prepared from NVF monomer or an interpolymer prepared from NVF monomer and a vinyl monomer. The hair care composition also include an ingredient selected from the group consisting of a conditioning agent, an emulsifier, a surfactant, a viscosity modifier, a gelling agent, an opacifier, a stabilizer, a preservative, a sequestering agent, a chelating agent, a pearling agent, a clarifying agent, a fragrance, a colorant, a propellant, water and an organic solvent. The polymer is present in amounts effective to provide the inventive hair care composition with hair fixative properties and/or with hair conditioning properties. The invention also relates to methods of treating hair which comprise applying to the hair the hair care compositions of the present invention.

DETAILED DESCRIPTION OF THE INVENTION

N-vinyl formamide (NVF) polymerizes to form a nonionic, water-soluble polymer which has a Tg of about 147° C. and which forms clear, non-tacky films upon drying. The present invention is directed to hair care compositions which utilize water-soluble polymers which are prepared from N-vinyl formamide. N-vinyl formamide monomer is available from Air Products and Chemicals, Inc., Allentown, Pa., under the trade name Vinamer™ EF. Processes for preparing N-vinyl formamide are disclosed in U.S. Pat. Nos. 4,578,515, 4,906,777, 4,942,259 and 5,037,927, all of which are hereby incorporated by reference in their entirety. In the present invention, NVF is not hydrolyzed prior to preparation of the hair conditioning polymer.

An indication of the relative water solubility of NVF versus PVP may be noted in the respective copolymers of vinyl acetate (VA). PVP/VA copolymers may contain up to 40 weight percent of VA and still yield clear solutions of the copolymer in water. On the other hand, NVF/VA copolymers containing greater than about 5 weight percent of VA do not yield such clear solutions, indicating that PVP is more soluble in water than NVF.

The polymer may be a homopolymer of N-vinyl formamide or may be an interpolymer prepared from N-vinyl formamide and at least one vinyl monomer(s). Preferably, the interpolymer will comprise at least about 10 weight percent of NVF, with the balance of the vinyl monomer(s). The term "vinyl monomer", as used herein, refers to vinyl monomers which are copolymerizable with the N-vinyl formamide. Suitable vinyl monomers include, (a) styrene and derivatives thereof, (b) $C_1-C_{18}$ alkyl esters of acrylic acid, (c) $C_1-C_{18}$ alkyl esters of methacrylic acid, (d) vinyl esters of the formula $CH_2=CH-OCOR$ where R is $C_1-C_{18}$, (e) alkyl substituted acrylamides and methacrylamides of the formula $CH_2=CR-CONR_1R_2$ where R is H or $CH_3$, $R_1$ is H or $C_1-C_{12}$ and $R_2$ is $C_1-C_{18}$, (f) monoesters and diesters of fumaric, itaconic and maleic acids, (g) vinyl ethers such as methyl vinyl ether, isobutyl vinyl ether and the like, (h) hydroxy functional acrylates and methacrylates such as hydroxyethyl acrylate, hydroxypropyl acrylate, hydroxyethyl methacrylate, hydroxypropyl methacrylate and the like, (i) vinyl monomers containing an amine selected from the group consisting of secondary, tertiary and quaternary amines, such as t-butylaminoethyl methacrylate (t-BAEM), dimethylaminoethyl methacrylate (DMAEMA), diethylaminoethyl methacrylate (DEAEMA), dimethylaminopropyl methacrylate (DMAPMA) and the quarternized derivatives thereof such as methacrylatoethyltrimethyl ammonium chloride (MAPTAC), methacrylatoethyltrimethyl ammonium sulfate (MAETAS) and dimethyl diallyl ammonium chloride (DMDAAC), (j)acrylamide, (k)non-alkyl substituted acrylamides such as diacetone acrylamide, and (l) cyclic amides such as vinyl pyrrolidone. Preferably, the vinyl comonomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, and the vinyl monomers containing an amine selected from the group consisting of secondary, tertiary and quaternary amines.

In order to function as a hair fixative, the hair care composition and the hair fixative resin, i.e., the NVF polymer, must possess certain hair fixative properties. For instance, the compositions must be capable of forming flexible, clear, low-tack or non-tacky films at room temperature. Once applied to the hair, the films must possess sufficient stiffness and humidity resistance to hold the hair in place under conditions normally encountered by the user thereof, yet must be readily removable from the hair by conventional shampoos and/or water. The polymer will preferably have a glass transition temperature (Tg) which is effective to form clear, low tack or non-tacky films at room temperature. If the Tg is too low, the films formed may be too tacky and may not possess adequate stiffness and humidity resistance.

Gel fixatives according to the present invention comprise as a hair fixative resin a homopolymer which is prepared from N-vinyl formamide, or interpolymers prepared from N-vinyl formamide and at least one vinyl monomer(s). The gel fixatives preferably are substantially free of organic hydrocarbon solvents and natural or synthetic oils, such as glycerol esters of higher even-numbered fatty acids, glycerides of palmitic stearic and oleic acid, liquid fatty acid esters, liquid fatty alcohols, paraffin oils, esters of polyhydric alcohols and polyethylene alcohols.

The hair fixative gels of the invention comprise an amount of the hair fixative polymer which is effective to impart hair fixative properties to the gels. Where the level of polymer is too high, the gels and films formed therefrom exhibit unacceptable haziness. Where the level of polymer is too low, properties such as stiffness and humidity resistance are adversely affected. Typically, the gels comprise from about 0.5 to about 15 weight percent of the polymer, preferably from about 1 to about 10 weight percent, and more preferably from about 2 to about 7 weight percent of the polymer, based on the total weight of the gel. The hair fixative gels also comprise a gelling agent in amounts effective to form a gel. Preferably, the gels comprise from about 0.05 to about 3 weight percent of the gelling agent, more preferably from about 0.1 to about 1.0 weight percent of the gelling agent, based on the total weight of the hair fixative gel. Examples of such gelling agents include synthetic polymers such as the acrylic-based Carbopol® series of thickeners available from B.F. Goodrich, Cleveland, Ohio and associative thickeners such as Aculyn™, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In certain embodiments, the rheology will be such that the gels may be applied via a spray pump. That is to say, the gels will be shear thinning to the extent that they may be applied via a spray pump and retain their hair fixative properties once applied to the hair. As one skilled in the art will appreciate, the particular rheological properties required for a spray pump application may be dependent upon factors such as the spray nozzle utilized, gel composition, the organic solvent system utilized, if any, and the like. One skilled in the art, having the benefit of the teachings of the present invention, will be able to ascertain the particular rheological properties required for a particular spray pump application.

In other embodiments, the hair fixative compositions may be in the form of an aerosol or non-aerosol spray, a mousse or a hair-setting lotion. The compositions may be aqueous, i.e. they are substantially free of organic solvents, or non-aqueous, although aqueous hair fixative compositions are preferred. The compositions may contain up to 40 weight percent, preferably up to 35 weight percent, of propellants, such as ethers, compressed gases, halogenated hydrocarbons and hydrocarbons. Exemplary propellants are dimethyl ether, propane, butane and 1,1-difluoroethane. Non-aqueous hair fixative compositions may further include solvents such as ethanol, isopropanol, acetone, dimethoxymethane and methyl ethyl ketone. The compositions may further include other materials or additives such as fragrances, preservatives, colorants, plasticizers, emulsifiers, conditioners, neutralizers, glossifiers and the like. Such propellants, solvents and materials or additives are commonly used in hair fixative compositions known heretofore.

Mousses according to the present invention comprise an amount of the polymer which is effective to impart hair fixative properties to the mousse, similar to gel fixatives. The mousses further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation—Nonoxynol 15) and Brij 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water.

In order to function as a hair conditioner, the hair care composition must possess certain hair conditioning properties. Such properties include, for example, substantivity of the conditioning agent on the hair without excessive build-up and enhancement of hair manageability, i.e., wet combability, dry combability, neutralization of static charge generated by combing and ease of styling. Other properties include lubrication of the hair to reduce friction between hair and comb and to minimize tangling. The additive should also soften the hair and impart gloss to dull hair and smooth the feel of the hair by filling in gaps or flattening cuticle scales. It is also advantageous for the hair conditioner to improve set retention of the hair.

In order to provide the hair care compositions with hair conditioning properties, the inventive polymers comprise the polymerized residue of the vinyl monomer containing at least one amine group selected from the group consisting of secondary, tertiary and quaternary amines, in amounts effective to provide the hair care compositions with hair conditioning properties. Particularly preferred vinyl monomers which contain the amine group are the quaternary amine-containing monomers. Suitable monomers containing a quaternary amine include, for example, methacrylatoethyltrimethyl ammonium sulfate (MAETAS), methacrylamidopropyltrimethyl ammonium chloride (MAPTAC) and dimethyl diallyl ammonium chloride (DMDAAC). Preferred quaternary amine-containing moieties are MAPTAC and DMDAAC.

The secondary and tertiary amines may be nonionic or cationic, although cationic amines are preferred. In certain embodiments, nonionic secondary and tertiary amines, such as t-butyl aminoethyl methacrylate (t-BAEM), dimethylaminoethyl methacrylate (DMAEMA) and dimethylaminopropyl methacrylamide (DMAPMA) are converted to cationic amines. One method for such conversion is to neutralize the secondary or tertiary amines with an appropriate acid to form an ammonium salt. Alternatively, the secondary or tertiary amines may be reacted with quaternizing agents to form quaternary amines. Such quaternizing agents include, for example, alkyl halides such as methyl chloride, or dialkyl sulfates such as dimethyl sulfate. One skilled in the art will recognize that there may be other routes to convert the nonionic secondary and tertiary amines to cationic amines. Suitable monomers containing a nonionic tertiary amine include, for example, DMAEMA and DMAPMA. Suitable monomers containing a nonionic secondary amine include, for example, t-BAEM.

In embodiments exhibiting hair conditioning properties, the polymer may be a copolymer comprising the residue of N-vinyl formamide and the residue of the vinyl amine-containing monomer. Preferably, the copolymer comprises from about 50 to about 99 weight percent of the residue of NVF and from about 1 to about 50 weight percent of the residue of the vinyl amine-containing monomer. More preferably, the copolymer comprises from about 60 to about 90 weight percent of the residue of NVF and from about 30 to about 10 weight percent of the residue of the vinyl amine-containing monomer. Most preferably, the copolymer comprises from about 75 to about 90 weight percent of the residue of NVF and from about 25 to about 10 weight percent of the residue of the vinyl polymerizable moiety.

The hair conditioning compositions of the present invention comprise an amount of the hair conditioning polymer which is effective to impart hair conditioning properties to the hair conditioning compositions. Typically, the hair conditioning compositions comprise from about 0.1 to about 15 weight percent of the polymer, preferably from about 0.25 to about 10 weight percent of the polymer, based on the total weight of the hair conditioning composition.

In one embodiment, the hair conditioning composition is a conditioning lotion. In addition to the inventive conditioning polymer, the lotion may further comprise other conditioning agents, such as cationic surfactants, fatty acid salts, hydrolyzed proteins such as collagen, keratin and amino acids, and oily materials such as lanolin, fatty alcohols, waxes and botanical oils. The lotion may also further comprise other ingredients such as emulsifiers, viscosity modifiers, opacifiers, pearlizers, stabilizers, preservatives, fragrances and colorants. In certain embodiments, the lotion may be applied via a spray delivery system.

In other embodiments, the hair conditioning composition is a conditioning shampoo. The shampoos generally comprise primary surfactants for cleansing and foam, secondary surfactants for cleansing, foam boosting and conditioning and additional additives for special performance, stability, fragrance and color. More specifically, these aqueous-based systems may contain surfactants, conditioning agents such as cationic or amphoteric surfactants, oily materials, proteins, botanicals, synthetic resins and silicone polymers, in addition to other additives such as sequestering or chelating agents, viscosity modifiers, opacifying, pearling or clarifying agents, stabilizers, fragrances, colorants and preservatives.

The hair conditioning composition also may comprise a gelling agent in amounts effective to form a conditioning gel. Preferably, the conditioning gel comprises from about 0.05 to about 3 weight percent of the gelling agent, more preferably from about 0.1 to about 1.0 weight percent of the gelling agent, based on the total weight of the conditioning gel. Examples of such gelling agents include synthetic polymers such as the acrylic-based Carbopol® series of thickeners available from B.F. Goodrich, Cleveland, Ohio and associative thickeners such as Aculyn™, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum.

In yet other embodiments, the hair conditioning composition may be in the form of mousse or spray. The mousse or spray may contain, in addition to the ingredients mentioned herein above, up to 40 weight percent, preferably up to 35 weight percent, of propellants such as ethers, compressed gases, halogenated hydrocarbons and hydrocarbons. Exemplary propellants are dimethyl ether, propane, butane, 1,1-difluoroethane, and mixtures thereof. The mousses further comprise from about 0.25 to 6 weight percent, preferably 0.25 to 3 weight percent, of an emulsifier. The emulsifier may be nonionic, cationic, anionic or amphoteric.

Exemplary nonionic emulsifiers include Tergitol® NP 15 (INCI designation—Nonoxynol 15) and Brig 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water.

The hair conditioning compositions may include organic solvents to modify certain properties of the hair conditioning compositions, such as viscosity, solubility or drying. Typical solvents include, for example, ethanol, isopropanol, acetone, dimethoxymethane and methyl ethyl ketone. When used, the amounts of organic solvents preferably are less than about 40 weight percent, more preferably less than about 30 weight percent and even more preferably are minimized. Most preferably, the compositions will be free of organic solvents.

The hair care compositions will contain from about 0.1 to about 20 weight percent of an ingredient selected from the group consisting of conditioning agents, emulsifiers, surfactants viscosity modifiers, gelling agents, opacifiers, stabilizers, preservatives, sequestering agents, chelating agents, pearling agents, clarifying agents, fragrances and colorants. Preferably, the composition will comprise from about 1 to about 10 weight percent of the one or more ingredients.

The invention is also directed to methods of treating hair which comprise applying to the hair an the hair care composition which comprises the polymer of the present invention in amounts effective to provide the hair care composition with a property selected from the group consisting of a hair fixative property and a hair conditioning property, as those properties are discussed herein, and an ingredient selected from the group consisting of conditioning agents, emulsifiers, surfactants viscosity modifiers, gelling agents, opacifiers, stabilizers, preservatives, sequestering agents, chelating agents, pearling agents, clarifying agents, fragrances, colorants, and propellants.

The following examples are indicative of preferred hair care compositions and hair care polymers utilized therein. They are not intended and should not be construed to limit the scope of the claims appended hereto. All percentages noted herein are weight percent unless noted otherwise. With the exception of Polymer L, inherent viscosities (I.V.) were determined on 1 weight percent polymer in 1N KCL aqueous solutions. The I.V. of Polymer L was determined on 1 weight percent polymer in water.

EXAMPLES

Preparation of NVF Homopolymers by Solution Polymerization

Into a 2-liter flask equipped with a stirring shaft powered by a mechanical stirrer, a water bath, a thermometer and a reflux condenser were added as an initial charge 22.5 grams of NVF, 53.5 grams of a 70:30 ethanol/water mixture (wt %), 25.0 grams of water and 1.12 grams of t-butyl peroctoate. The mixture was brought to reflux to allow formation of a solvent atmosphere blanket above the reagents. After 15 minutes of reflux, a monomer slow-add of a mixture of 177.5 grams NVF and 270 grams of water was continuously and regularly added over a 4 hour period. Two hours after the beginning of the monomer slow-add, a mixture of 26.5 grams of a 70:30 ethanol/water (wt %) and 0.2 gram of t-butyl peroctoate was added regularly and continuously over a 2 hour period. When the above slow-adds had been introduced, a post-scavenging slow-add composed of 37 grams of a 70:30 ethanol/water mixture (wt %) and 0.66 gram of t-butyl peroctoate was added regularly and continuously over a 3 hour period. This was followed by a 5 hour hold period during which reflux was also maintained. After cooling, the apparatus was modified to include a Dean-Stark trap. The organic solvent was distilled off, steam being introduced above the reaction mixture when the vapor temperature reached about 90° C. When the reflux temperature had reached 100° C, steam was injected subsurface and the operation maintained for 15 minutes. The aqueous solution appeared clear and was diluted to 20% solids content. The polymer had an I.V. of 1.61 and was designated Polymer A.

A second NVF homopolymer was prepared according the above procedure, except that 0.6 gram of beta-mercaptoethanol was included in the first monomer slow-add. The final aqueous solution appeared clear and was diluted to 20.4% solids. The polymer had an I.V. of 0.68 and was designated Polymer B.

Preparation of NVF Homopolymer by Precipitation Polymerization

The same apparatus was used as was described in Example. Into the flask was introduced an initial charge comprising 22.5 grams of NVF, 279 grams of ethyl acetate, and 1.12 grams of t-buty peroctoate. The mixture was brought to reflux to allow formation of a solvent atmosphere blanket above the reagents. After 15 minutes of reflux, a monomer slow-add comprising 177.5 grams of NVF and 330 grams of ethyl acetate was added regularly and continuously over a 4 hour period, refluxing conditions being maintained. Two hours after initiation of the above slow-add, a mixture of 26.5 grams of ethyl acetate and 0.2 gram of t-butyl peroctoate was added regularly and continuously over a 2 hour period. When the above slow-adds were completed, a post scavenging slow-add composed of 37 grams of ethyl acetate and 0.66 grams of t-butyl peroctoate was added regularly and continuously over a 3 hour period, refluxing conditions being maintained. The reactants were allowed to reflux for 5 hours. After cooling, the suspension was vacuum filtered and washed with ethyl acetate. The resulting white particles were dried overnight at 60° C. The polymer had an I.V. of 3.88 and was designated Polymer C.

Preparation of NVF Terpolymer by Precipitation Polymerization

A terpolymer comprising 78 weight percent NVF, 15 weight percent HPA and 7 weight percent MA was prepared in a similar precipitation polymerization procedure as was used to prepare the NVF homopolymer. The terpolymer was designated Polymer P.

Preparation of NVF/(meth)acrylate(s) Copolymer by Solution Polymerization

The following recipe is given for 200 grams of a copolymer of composition X% NVF and Y% (meth)acrylate.

Into a 2 liter flask equipped with a stirring shaft powered by a mechanical stirrer, a water bath, a thermometer and a reflux condenser were introduced as the initial charge 22.5 grams of monomers, so that the percent of (meth)acrylate monomer is $Y \times 2/3$; 53.5 grams of a 70:30 ethanol/water mixture (wt %), 10 grams of water and 1.12 grams of t-butyl peroctoate. The mixture was brought to reflux to allow formation of a solvent atmosphere blanket above the reagents. After 15 minutes of reflux, a monomer slow-add of a mixture of 113.2 grams of monomers so that the percent of (meth)acrylate monomer is Y and 190 grams of water were regularly and continuously added over a 3 hour period. Two hours after the beginning of the monomer slow-add, a mixture of 26.5 grams of a 70:30 ethanol/water (wt %) and 0.2 gram of t-butyl peroctoate was added regularly and continuously over a 2 hour period. When the first monomer slow-add was completed, it was immediately followed by a second monomer slow-add containing the remaining 64.3 grams of monomers and 60 grams of water, which was added regularly and continuously over a one hour period. When the above slow-adds had been introduced, a post-scavaging slow-add composed of 37 grams of a 70:30 ethanol/water mixture (wt %) and 0.66 gram of t-butyl peroctoate was added regularly and continuously over a 3 hour period. This was followed by a 5 hour hold period during which reflux was also maintained. After cooling, the apparatus was modified to include a Dean-Stark trap. The organic solvent was distilled off, steam being introduced above the reaction mixture when the vapor temperature reached about 90° C. When the reflux temperature had reached 100° C., steam was injected subsurface and the operation maintained for 15 minutes.

The following copolymers were prepared using the above procedure:

Polymer D: 90 NVF/10 HPA. The final aqueous solution appeared translucent and had an I.V. of 1.80.

Polymer E: 95 NVF/5 MA. The final aqueous solution appeared clear and had an I.V. of 1.40.

Polymer F: 90 NVF/10 HEA. The final aqueous solution appeared slightly translucent and had an I.V. of 1.44.

Polymer G: 90 NVF/10 HEMA. The final aqueous solution appeared translucent and had an I.V. of 1.25.

Polymer H: 95 NVF/5 HEM-5. The final aqueous solution appeared clear and had an I.V. of 1.74.

Polymer I 95 NVF/5 MMA. The final aqueous solution appeared translucent and had an I.V. of 2.35.

Polymer J: 90 NVF/10 HPMA. The final aqueous solution appeared opaque and had an I.V. of 2.48.

Polymer K: 85 NVF/15 HPA. The final aqueous solution appeared translucent and had an I.V. of 1.38.

HEA=2-hydroxyethyl acrylate
HPA=2-hydroxypropyl acrylate
MA=methyl acrylate
HEMA=2-hydroxyethyl methacrylate
HPMA=2-hydroxypropyl methacrylate
MMA =methyl methacrylate
HEM-5=oligoethylene glycol monomethacrylate
(obtained from Rhone-Poulenc under the trade name Sipomer HEM-5)

Preparation of NVF/vinyl acetate (VA) copolymers by Solution Polymerization Into a 2-liter flask equipped with a stirring shaft powered by a mechanical stirrer, a water bath, a thermometer and a reflux condenser were added as an initial charge 12.5 grams of NVF, 10 grams of vinyl acetate, 63.5 grams of a 70:30 ethanol/water mixture (wt %), 10 grams of water and 1.12 grams of t-butyl peroctoate. The mixture was brought to reflux to allow formation of a solvent atmosphere blanket above the reagents. After 15 minutes of reflux, a monomer slow-add of a mixture of 177.75 grams NVF and 250 grams of water were added regularly and continuously over a 4 hour period. Two hours after the beginning of the monomer slow-add, a mixture of 26.5 grams of a 70:30 ethanol/water (wt %) and 0.2 gram of t-butyl peroctoate was added regularly and continuously over a 2 hour period. When the above slow-adds had been introduced, a post-scavaging slow-add composed of 37 grams of a 70:30 ethanol/water mixture (wt %) and 0.66 gram of t-butyl peroctoate was added regularly and continuously over a 3 hour period. This was followed by a 5 hour hold period during which reflux was also maintained. After cooling, the apparatus was modified to include a Dean-Stark trap. The organic solvent was distilled off, steam being introduced above the reaction mixture when the vapor temperature reached about 90° C. When the reflux temperature had reached 100° C., steam was injected subsurface and the operation maintained for 15 minutes. The final aqueous solution appeared clear, had an I.V. of 0.95 and was designated Polymer L.

The following NVF/vinyl acetate copolymers were prepared according to the above procedure, adjusting the monomers according to the relative percentages.

Polymer M: 78 NVF/22 VA. The final aqueous solution appeared very yellow and opaque.

Polymer N: 50 NVF/50 VA. The final aqueous solution appeared opaque and yellowish.

Polymer 50 NVF/50 VA. The final copolymer appeared to be a white fluid.

Preparation of Gel Compositions

Polymers A through O were formulated into hair fixative gel compositions according to the following formulation. All values reported are parts by weight, based on the total weight of the gel composition.

|  | Ingredient | Parts by Weight |
|---|---|---|
| Part A | NVF polymer | 3.00 |
|  | triethanolamine (TEA) | 0.60 |
|  | deionized water | 47.85 |
| Part B | Carbopol ® 940 | 0.6 |
|  | Dowicil ® 200 (preservative) | 0.10 |
|  | deionized water | 47.85 |
|  |  | 100 |

The polymer and TEA were mixed in D.I. water until homogenous. In a separate vessel, the Dowicil® 200 preservative and Carbopol® 940 thickener were combined with D.I. water and mixed until the Carbopol® went into solution. Dowicil® 200 is available from The Dow Chemical Company, Midland, Mich. Parts A and B were then combined and mixed gently until a clear viscous gel was formed.

High Humidity Curl Retention Test Protocol

Each of the gels was tested on nine dampened 10-inch swatches of European Brown hair. To each swatch was applied 0.5 g of the respective gel composition. The gel was worked into the swatch, which then was curled end-over-end on a 0.5 inch teflon mandrel. The curl was then carefully removed from the mandrel and secured with two hair clips. The curl was then placed in an oven at a temperature of 120° F. overnight. The dried curl was gently unwound and hung on a graduated, transparent curl retention board contained in a humidity chamber at 90% relative humidity and 70° F. Percent curl retention was measured at 15, 30, 60, 90 and 120 minutes. Curl retention is calculated as below. The mean % retention obtained at each time interval are compared, statistically analyzed and reported at the 95% confidence level.

$$\text{Curl Retention} = \frac{L - L_t}{L - L_o} \times 100$$

L=Length of swatch fully extended
$L_o$=Length of curl before exposure
$L_t$=Length of curl after exposure Stiffness Test Protocol Each of the gels was tested on three dampened 4.5 inch Brown Virgin Italian hair swatches. To each swatch was applied 0.25 g of the respective gel. The gel was worked into the swatch and each swatch dried in an oven at 110° F. for two hours. The swatches were placed in a constant temperature and humidity chamber at 50% relative humidity and 23° C. and allowed to remain therein overnight. The stiffness of the swatches were measured using appropriate device for measuring stiffness. The results were statistically analyzed and reported at the 95% confidence level.

EXAMPLE 1

Gels formulated with Polymers A, B, D, E, F and G were compared for high humidity curl retention and stiffness to PVP K-90 gels which were formulated with the Carbopol® 940 thickener. PVP K-90 is a homopolymer of vinyl pyrrolidone available from International Specialty Products, Wayne, N.J. Results are reported in Table 1.

TABLE 1

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFFNESS |
| POLYMER A | 94.85 | 82.34 | 74.60 | 59.15 | 56.24 | 364 |
| POLYMER B | 88.89 | 78.18 | 60.23 | 47.89 | 44.11 | 401 |
| POLYMER D | 91.36 | 82.06 | 71.12 | 60.64 | 57.98 | 416 |
| POLYMER E | 95.22 | 90.74 | 79.18 | 68.55 | 62.84 | 382 |
| POLYMER F | 89.48 | 83.37 | 73.65 | 64.70 | 59.92 | 388 |
| POLYMER G | 93.07 | 86.78 | 78.86 | 66.13 | 62.75 | 360 |
| PVP K-90 | 89.76 | 82.23 | 76.23 | 67.39 | 63.31 | 345 |

As the high humidity curl retention results indicate, there is no statistically significant differences between gels formulated with Polymers A, D, E, F, and G and the PVP K-90 comparative example gel. The gel formulated with Polymer B appeared to be inferior to the PVP K-90 gel.

With respect to stiffness, gels formulated with Polymers B, D and F were statistically superior to the PVP K-90 gel, with the remaining gels showing no statistically significant differences.

Gels formulated with Polymers A through F exhibited improved clarity over the PVP K-90 gel, while the get formulated with Polymer G was less clear than the PVP K-90 gel.

EXAMPLE 2

Gels formulated with Polymers M, N and O were compared to the PVP K-90 gets as above. Results are reported in Table 2.

TABLE 2

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFFNESS |
| POLYMER M | 84.94 | 73.54 | 53.98 | 49.30 | 47.32 | 355 |
| POLYMER N | 83.55 | 69.16 | 51.27 | 45.72 | 42.56 | 295 |
| POLYMER O | 84.76 | 70.57 | 57.67 | 52.47 | 49.65 | 307 |
| PVP K-90 | 85.20 | 69.14 | 54.78 | 49.77 | 44.81 | 356 |

There are no statistically significant differences noted between gels formulated with Polymers M, N and O and the PVP K-90 comparative example.

Gels formulated with Polymers M exhibited comparable clarity to the PVP K-90 gel, while gels formulated with Polymers N and O were less clear than the PVP K-90 gel.

EXAMPLE 3

Gels formulated with Polymers C, H, I, J and L were compared to PVP K-90 as above. Results are reported in Table 3.

TABLE 3

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFFNESS |
| POLYMER C | 89.93 | 82.28 | 71.92 | 66.10 | 64.72 | 300 |
| POLYMER H | 90.14 | 84.23 | 73.00 | 67.19 | 64.71 | 282 |
| POLYMER I | 87.73 | 79.12 | 68.46 | 61.71 | 60.21 | 249 |

TABLE 3-continued

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFFNESS |
| POLYMER J | 89.35 | 82.16 | 75.25 | 70.46 | 68.79 | 315 |
| POLYMER L | 86.54 | 79.95 | 72.31 | 66.08 | 65.44 | 414 |
| PVP K-90 | 87.48 | 80.82 | 71.35 | 65.61 | 63.84 | 270 |

There were no statistically significant differences between any of the inventive gels and the comparative PVP K-90 gel with respect to high humidity curl retention.

The gel formulated with Polymer L was statistically superior to the PVP K-90 gel, while there were no statistically significant differences between the PVP K-90 gels and gels prepared with Polymers C, H, I and J with respect to stiffness.

Gels formulated with Polymers C and H exhibited improved clarity over the PVP K-90 gel. Gels formulated with Polymers I and J exhibited comparable clarity to the PVP K-90 gel, while gel the formulated with Polymer L was less clear than the PVP K-90 gel.

EXAMPLE 4

A gel formulated with Polymer K was compared to the PVP K-90 gels as above. Results are reported in Table 4.

TABLE 4

| | % HIGH HUMIDITY CURL RETENTION | | | | | |
|---|---|---|---|---|---|---|
| | 15 MIN. | 30 MIN. | 60 MIN. | 90 MIN. | 2 HR. | STIFFNESS |
| POLYMER K | 94.15 | 88.81 | 77.11 | 58.67 | 42.21 | 260 |
| PVP K-90 | 91.21 | 80.49 | 61.62 | 45.55 | 36.19 | 203 |

Both curl retention and stiffness of the gel formulated with Polymer K were statistically superior to the PVP K-90 control gel.

The gel formulated with Polymer K exhibited improved clarity over the PVP K-90 gel.

Polymers C, K and Q (herein below) were formulated into the following mousse composition and evaluated for stiffness as noted above in comparison to a similar mousse containing the PVP K-90 polymer.

| Ingreident | Parts by Weight |
|---|---|
| NVF Polymer | 2.50 (dry weight) |
| Tergitol ® NP15 surfactant | 0.50[1] |
| Brij ® 97 surfactant | 0.30 |
| Dowicil ® 200 preservative | 0.10 |
| Propellant (20:80/Propane:butane) | 10.00 |
| Water | 86.60 |
| | 100.00 |

[1]mousse containing Polymer P 0.75% Tergitol; 86.35% water.

The mousse formulated with Polymer Q (299 stiffness) was statistically superior to that formulated with PVP K-90 (228 stiffness), while there was no significant difference noted between mousses formulated with Polymers K (219 stiffness ) and C (223 stiffness) and the PVP K-90 polymer.
Polymer Preparation by Solution Polymerization:

The polymers were prepared in 4-neck, 2-L flasks equipped with a stirring shaft powered by a mechanical stirrer, 2 addition funnels, water bath, thermometer and reflux condenser. In the flask were introduced the initial charge of 18 g of NVF, 4.5 g of a 53.0% aqueous solution of MAPTAC, 53.5 g of a 70:30 ethanol/water mixture (wt %), 10 g of water, and 1.12 g of t-butyl peroctoate. The mixture was brought to reflux to allow formation of a solvent atmosphere blanket about the reagents. After 15 min of reflux, a monomer slow-add of the following composition was regularly and continuously added over a period of 4 hours, the refluxing conditions being maintained: 142 g NVF, 35.5 g of a 53.0% aqueous solution of MAPTAC and 235 g of water. Two hours after the beginning of the above addition, a mixture of 26.5 g of a 70:30 ethanol/water mixture (wt %) and 0.2 g of t-butyl peroctoate was regularly and continuously added over a period of 2 hours. When the above slow-adds had been introduced a post-scavenging slow-add composed of 37 g of a 70:30 EtOH/water mixture (wt %) and 0.66 g of t-butyl peroctoate was added regularly and continuously over a period of 3 hours, refluxing conditions being maintained. This was followed by a hold period of 5 hours during which reflux was also maintained. After cooling, the setup was modified by the incorporation of a Dean-Stark trap. The organic solvent was distilled off, steam being introduced above the reaction mixture when the vapor temperature had reached 90° C. When the reflux temperature had reached 100° C., steam was injected subsurface and the operation maintained for 15 min.

The final aqueous solution appeared clear and was diluted to 19.4% solids content. The polymer was designated Polymer R (NVF 88/MAPTAC 12). The final polymer had a inherent viscosity of 1.27 dl/g$^{-1}$. Inherent viscosity (I.V.) was determined on 1 wt % polymer in 1N KCl aqueous solutions. GPC analysis was performed at 80° C. in 0.03N NaNO$_3$ DMSO solutions. Dextrans were used as standards. GPC analysis gave the following data:

$Mn = 6.3 \times 10^4$; $Mw = 3.9 \times 10^5$; $Ip$ (polydispersity, i.e., $Mw/Mn) = 6.3$.

The following copolymers were prepared using the above procedure, the amount of monomer used being calculated to meet the formulated final composition:

Polymer Q: NVF 80/MAPTAC 20

Polymer S: NVF 80/DMDAAC 20

Procedures for Evaluation of Conditioning Compositions:

Polymers Q-R were evaluated against a control as a hair-conditioning additive with respect to the following properties: wet combability, dry combability, gloss, presence of static flyaway, flakiness and feel. Details of the test are described below.

The polymers were evaluated as 2% active aqueous solutions and compared to a control consisting of water. Virgin dark brown hair was obtained from DeMeo Brothers, 129 W. 28th Street, New York, N.Y. 10001. A separate 5.25 gram hair swatch, 10" in length, was used for each polymer or water treatment.

Swatches were saturated with tepid water. Excess water was removed by squeezing the wet swatch between the thumb and index finger. Five drops of the test solution were dropped along the length of the swatch and were worked into the swatch using 10 (ten) downward strokes. The swatch samples were grouped as pairs (polymer-treated versus water-treated). A total of eight pairs of samples were evaluated. Performance was evaluated by a trained panel of four members, who compared the coded, inventive polymers to a control of only water. Each member on the panel rated two pairs of samples (polymer vs. water) as being inferior/superior (±) one to the other, or as no statistical difference (NS). Eight pairs in all were tested for each polymer. Each swatch was evaluated as follows:

1. Wet combability—The swatch was gently combed several times and rated for ease of comb-out.

After drying for one hour at 120° F., the following properties were evaluated:

2. Gloss—The swatch was visually rated for gloss and sheen.
3. Stiffness—The swatch was handled by the panelist and rated for stiffness versus softness according to the resistance felt when attempting to bend the hair swatch.
4. Dry Combability—The swatch was gently combed several times and rated for ease of comb-out.
5. Flakiness—The swatch was visually examined for flaking following combing.
6. Static flyaway—The swatch was vigorously combed and then rated for the extent of static flyaway exhibited.
7. Feel—The swatch was evaluated for tactile properties by the panelist.

Data acquired from these methods are qualitative and not quantitative, and therefore subjective. However, panelists who participated in these blind studies have been trained in the analysis of hair swatches for these properties. Additionally, the subjective evaluations are statistically analyzed to identify differences at the 90% confidence level. Results of the evaluation are found in Table 1.

TABLE 1

| Property | Polymer Q | Polymer R | Polymer S |
|---|---|---|---|
| Wet Combability | + | NS | + |
| Gloss | + | + | NS |
| Stiffness | + | + | + |
| Dry Combability | − | − | − |
| Flakiness | − | − | − |
| Static Flyaway | − | − | NS |
| Feel | NS | NS | NS |

As the results indicate, NVF/MAPTAC Polymers Q and R exhibit hair conditioning properties, such as improved hair gloss and stiffness, while Polymer Q exhibited improved wet combability. Additionally, although not statistically different (NS) under the test criteria, a majority of the samples utilizing Polymer R were found to improve wet combability. The NVF/DMDAAC Polymer S was found to improve wet combability and stiffness. Additionally, although not statistically different under the test criteria, a majority of the panelists found Polymer S to improve static flyaway and the feel of the hair. As indicated herein, additional vinyl monomers may be used in combination with the NVF monomer and the vinyl polymerizable moiety to modify or improve certain hair conditioning properties of the of the conditioning compositions.

The following are hair conditioning formulations in which the inventive hair conditioning polymers may be used. As one skilled in the art will recognize, once armed with the present specification, the formulations are not inclusive of all conditioning formulations anticipated by the present invention. Additionally, each class of conditioner represented by the formulations may include other ingredients such as those discussed herein above. Parts by weight of the conditioning polymer are on a dry weight basis.

Hair Conditioning Formulations:
Conditioning Lotion:

| Ingredient | Parts by weight |
|---|---|
| NVF Polymer | 1.00 |
| Carbopol® 940 thickener | 0.15 |
| Triethanolamine | 0.15 |
| Deionized Water | 98.70 |
| | 100.00 |

Procedure: The Carbopol® 940 thickener is dispersed in water with good agitation. The conditioning polymer is added to the water and mixed until dissolved. While mixing, triethanolamine is added. Mixing is continued until a homogeneous mixture is produced.

Conditioning Shampoo

| Ingredient | Parts by weight |
|---|---|
| NVF Polymer | 1.80 |
| TEA Lauryl Sulfate | 25.00 |
| Cocamide DEA | 5.00 |
| Dowicil® 200 preservative | 0.10 |
| Deionized Water | 68.10 |
| | 100.00 |

Procedure: The conditioning polymer is dissolved in 20 parts water. In a separate container, the remaining water is heated to 70° C. TEA Lauryl Sulfate and Cocamide DEA are then added to the heated water. The polymer solution from step 1 is added to the heated water. The mixture is cooled to 40° C. and the preservative is added. The mixture is cooled to room temperature. Dowicil® 200 is available from The Dow Chemical Company, Midland, Mich.

Conditioning Gel

| | Ingredient | Parts by Weight |
|---|---|---|
| Part A | NVF Polymer | 3.00 |
| | Triethanolamine (TEA) | 0.60 |
| | Deionized Water | 47.85 |
| Part B | Carbopol® 940 thickener | 0.60 |
| | Dowicil® 200 preservative | 0.10 |
| | Deionized Water | 47.85 |
| | | 100.00 |

The polymer and TEA are mixed in D.I. water until homogenous. In a separate vessel, the Dowicil® 200 preservative and Carbopol® 940 thickener are combined with D.I. water and mixed until the thickener goes into solution. Parts A and B are then combined and mixed gently until a clear viscous gel is formed.

| Conditioning Mousse | |
| --- | --- |
| Ingredient | Parts by Weight |
| NVF Polymer | 2.50 |
| Tergitol® NP15 surfactant | 0.50 |
| Brij® 97 surfactant | 0.30 |
| Dowicil® 200 preservative | 0.10 |
| Propellant (20:80/Propane:butane) | 10.00 |
| Water | 86.60 |
| | 100.00 |

Procedure: The conditioning polymer is dissolved in water with adequate agitation. The surfactants and preservative are added and the solution is mixed until homogenous. The product is filtered and filled into a container. The container is then charged with the propellant. Tergitol® NP15 surfactant is available from Union Carbide Chemical and Plastics Company, Danbury, Conn. Brij® 97 surfactant is available from ICI Specialty Chemicals, Wilmington, Del.

In addition to the subjective, stiffness evaluation performed by the trained panel, Polymer Q was formulated into the above conditioning mousse formulation and compared to three comparative polymers, each of which also was formulated into the above mousse formulation. Comparative Polymers T and U are quaternary ammonium polymers formed by the reaction of diethyl sulfate and a copolymer of vinyl pyrrolidone and dimethyl aminoethylmethacrylate. Comparative Polymer V is a polyvinylpyrrolidone homopolymer. Each of the formulated mousses were tested on three dampened 4.5 inch Brown Virgin Italian hair swatches. To each swatch was applied 0.2 g of the respective mousse. The mousse was worked into the swatch and each swatch dried in an oven at 110° F. for two hours. The swatches were placed in a constant temperature and humidity chamber at 50% relative humidity and 23° C. and allowed to remain therein overnight. The stiffness of the swatches were measured using an appropriate device for measuring stiffness. The results were statistically analyzed and reported at the 95% confidence level. The mousse formulated with Polymer Q had a stiffness value 24% greater than that of a mousse formulated with Comparative Polymers T and V and 32% greater than a mousse formulated with Comparative Polymer U. Such differences are statistically significant. The improved stiffness is particularly important to conditioning gel, mousse and spray embodiments of the present invention.

We claim:

1. A hair care composition, comprising:
   from about 0.1 to about 15 weight percent of a polymer which is prepared via free-radical initiated polymerization, wherein the polymer is selected from the group consisting of a homopolymer prepared from N-vinyl formamide monomer and an interpolymer prepared from at least 10 weight percent N-vinyl formamide monomer, and a vinyl monomer; and
   an ingredient selected from the group consisting of a conditioning agent, an emulsifier, a surfactant, a viscosity modifier, a gelling agent, an opacifier, a stabilizer, a preservative, a sequestering agent, a chelating agent, a pearling agent, a clarifying agent, a fragrance, a colorant, a propellant, an organic solvent and water.

2. The hair care composition of claim 1 wherein the vinyl monomer is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$, (e) alkyl-substituted acrylamides and methacrylamides of the formula $CH_2$=CR—$CONR_1R_2$ where R is H or $CH_3$, $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) vinyl monomers containing an amine selected from the group consisting of secondary, tertiary and quaternary amines, (j) acrylamide, (k) non-alkyl-substituted acrylamides, and (l) cyclic amides.

3. The hair care composition of claim 1 wherein the composition is selected from the group consisting of a gel, a mousse, a lotion, a spray and a shampoo.

4. The hair care composition of claim 1 comprising from about 0.05 to about 3 weight percent of the gelling agent, thereby forming a gel.

5. The gel of claim 4 wherein the polymer comprises from about 100 to 10 weight percent of the residue of the N-vinyl formamide monomer and from 0 to about 90 weight percent of the residue of the vinyl monomer.

6. The gel of claim 5 wherein the gelling agent is selected from the group consisting of synthetic polymers, cellulosic thickeners, starch-based thickeners and naturally occurring gums.

7. The get of claim 5 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, methacrylatoethyltrimethyl ammonium chloride, methacrylatoethyltrimethyl ammonium sulfate and dimethyl diallyl ammonium chloride.

8. The gel of claim 5 wherein the polymer comprises from about 70 to about 90 weight percent of the residue of the N-vinyl formamide monomer and from about 30 to about 10 weight percent of the residue of the vinyl monomer selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, oligoethylene glycol monomethacrylate, methacrylatoethyltrimethyl ammonium chloride, methacrylatoethyltrimethyl ammonium sulfate and dimethyl diallyl ammonium chloride.

9. The hair care composition of claim 3 comprising from about 0.25 to about 6 weight percent of the emulsifier and from about 2.5 to about 25 weight percent of the propellant.

10. The hair care composition of claim 9 wherein the polymer comprises from about 100 to 10 weight percent of the residue of the N-vinyl formamide monomer and from 0 to about 90 weight percent of the residue of the vinyl monomer.

11. The hair care composition of claim 10 wherein the vinyl monomer is selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, vinyl acetate, oligoethylene glycol monomethacrylate, methacrylatoethyltrimethyl ammonium chloride, methacrylatoethyltrimethyl ammonium sulfate and dimethyl diallyl ammonium chloride.

12. The hair care composition of claim 10 wherein the polymer comprises from about 70 to about 90 weight percent of the residue of the N-vinyl formamide monomer and from about 30 to about 10 weight percent of the residue of the vinyl monomer selected from the group consisting of methyl acrylate, methyl methacrylate, 2-hydroxyethyl acrylate, 2-hydroxyethyl methacrylate, 2-hydroxypropyl acrylate, 2-hydroxypropyl methacrylate, oligoethylene glycol monomethacrylate, methacrylatoethyltrimethyl ammonium chloride, methacrylatoethyltrimethyl ammonium sulfate and dimethyl diallyl ammonium chloride.

13. The hair care composition of claim 1 wherein the polymer comprises the residue of the vinyl monomer containing an amine selected from the group consisting of secondary, tertiary and quaternary amines in an amount effective to provide the hair care composition with at least one hair conditioning property.

14. The hair care composition of claim 13 wherein the polymer comprises from about 1 to 50 weight percent of the residue of the vinyl monomer containing an amine group selected from the group consisting of secondary, tertiary and quaternary amines.

15. The hair care composition of claim 14 wherein the vinyl monomer containing an amine selected from the group consisting of a secondary, tertiary and quaternary amine is the quaternary amine selected from the group consisting of methacrylatoethyltrimethyl ammonium chloride, methacrylatoethyltrimethyl ammonium sulfate and dimethyl diallyl ammonium chloride.

16. A method for treating hair, the method comprising:

applying to the hair a hair care composition, which composition comprises:

from about 0.1 to about 15 weight percent of a polymer which is prepared via free-radical initiated polymerization, wherein the polymer is selected from the group consisting of a homopolymer prepared from N-vinyl formamide monomer and an interpolymer prepared from at least 10 weight percent N-vinyl formamide monomer, and a vinyl monomer; and an ingredient selected from the group consisting of a conditioning agent, a surfactant, a viscosity modifier, a gelling agent, an opacifier, a stabilizer, a preservative, a sequestering agent, a chelating agent, a pearling agent, a clarifying agent, a fragrance, a colorant, an organic solvent and water.

17. The method of claim 16 wherein the hair care composition comprises from about 0.05 to about 3 weight percent of the gelling agent.

18. The method of claim 16 wherein the hair care composition comprises from about 0.25 to about 6 weight percent of the emulsifier and from about 2.5 to about 25 weight percent of the propellant.

19. The method of claim 1 wherein the polymer comprises from about 100 to 10 weight percent of the residue of the N-vinyl formamide monomer and from 0 to about 90 weight percent of the residue of the vinyl monomer.

20. The method of claim 19 wherein the vinyl monomer is selected from the group consisting of (a) styrene and derivatives thereof, (b) $C_1$–$C_{18}$ alkyl esters of acrylic acid, (c) $C_1$–$C_{18}$ alkyl esters of methacrylic acid, (d) vinyl esters of the formula $CH_2$=CH—OCOR where R is $C_1$–$C_{18}$ (e) alkyl-substituted acrylamides and methacrylamides of the formula $CH_2$=CR—$CONR_1R_2$ where R is H or $CH_3$; $R_1$ is H or $C_1$–$C_{12}$ and $R_2$ is $C_1$–$C_{18}$, (f) monoesters and diesters of fumaric, itaconic and maleic acids, (g) vinyl ethers, (h) hydroxy functional acrylates and methacrylates, (i) vinyl monomers containing at least one amine group selected from the group consisting of secondary, tertiary and quaternary amines, (j) acrylamide, (k) non-alkyl-substituted acrylamides, and (l) cyclic amides.

21. The method of claim 20 wherein the polymer comprises from about 1 to about 50 weight percent of the residue of the vinyl monomer containing at least one amine group selected from the group consisting of secondary, tertiary and quaternary amines.

22. A hair care composition, comprising:

from about 0.1 to about 15 weight percent of a polymer, wherein the polymer is prepared via free-radical initiated polymerization and is selected from the group consisting of a homopolymer prepared from N-vinyl formamide monomer and an interpolymer prepared from at least 10 weight percent N-vinyl formamide monomer, and a vinyl monomer selected from the group consisting of styrene and derivatives thereof; $C_1$–$C_{18}$ alkyl esters of acrylic acid; $C_1$–$C_{18}$ alkyl esters of methacrylic acid; vinyl esters of the formula $CH_2$=CH—OCOR, where R is $C_1$–$C_{18}$; alkyl-substituted acrylamides and methacrylamides of the formula $CH_2$=CR—$CONR_1R_2$, where R is H or $CH_3$, $R_1$ is H or $C_1$–$C_{12}$, and $R_2$ is $C_1$–$C_{18}$; monoesters and diesters of fumaric, itaconic and maleic acids; vinyl ethers; hydroxy functional acrylates and methacrylates; vinyl monomers containing an amine selected from the group consisting of secondary, tertiary and quaternary amines; acrylamide; non-alkyl-substituted acrylamides; and cyclic amides; and an ingredient selected from the group consisting of a conditioning agent, an emulsifier, a surfactant, a viscosity modifier, a gelling agent, an opacifier, a stabilizer, a preservative, a sequestering agent, a chelating agent, a pearling agent, a clarifying agent, a fragrance, a colorant, a propellant, an organic solvent and water.

\* \* \* \* \*